United States Patent [19]

Shasha et al.

[11] Patent Number: 5,750,467
[45] Date of Patent: May 12, 1998

[54] LIGNIN-BASED PEST CONTROL FORMULATIONS

[75] Inventors: Baruch S. Shasha, Peoria; Michael R. McGuire, Metamora, both of Ill.; Robert W. Behle, Columbia, Md.

[73] Assignees: The United States of America as represented by the Secretary of Agriculture, Washington, D.C.; Biotechnnology Research & Development Corporation, Peoria, Ill.

[21] Appl. No.: 568,159

[22] Filed: Dec. 6, 1995

[51] Int. Cl.$^6$ .......................... A01N 25/04; A01N 25/10; A01N 25/24
[52] U.S. Cl. .......................... 504/116; 504/117; 424/408; 514/777; 514/972
[58] Field of Search .......................... 504/116; 424/408; 71/DIG. 1; 514/777, 972

[56] References Cited

U.S. PATENT DOCUMENTS

| | | | |
|---|---|---|---|
| 2,589,252 | 12/1952 | Heritage | 260/124 |
| 2,802,815 | 8/1957 | Doughty | 260/124 |
| 3,886,093 | 5/1975 | Dimitri | 252/447 |
| 3,929,453 | 12/1975 | Dimitri et al. | 71/101 |
| 3,958,007 | 5/1976 | Wommack, Jr. | 424/300 |
| 4,069,217 | 1/1978 | Detroit et al. | 260/124 |
| 4,075,332 | 2/1978 | Oswald et al. | 424/216 |
| 4,184,866 | 1/1980 | Dellicolli et al. | 71/65 |
| 4,244,729 | 1/1981 | Dellicolli et al. | 71/65 |
| 4,381,194 | 4/1983 | DelliColli et al. | 71/65 |
| 4,911,952 | 3/1990 | Doane et al. | 427/213 |
| 4,971,989 | 11/1990 | Jensen-Korte | 514/404 |
| 5,061,697 | 10/1991 | Shasha et al. | 514/60 |
| 5,332,584 | 7/1994 | Scher et al. | 424/408 |
| 5,552,149 | 9/1996 | Lebo, Jr. et al. | 424/408 |

FOREIGN PATENT DOCUMENTS

| | | | |
|---|---|---|---|
| WO 92/19102 | 5/1992 | WIPO | A01N 25/28 |
| WO 95/22253 | 8/1995 | WIPO | A01N 25/22 |

OTHER PUBLICATIONS

A Guide To Agriculture Spray Adjuvants Used In The United States, by Lori Thomson Harvey, 1988–1989 Edition.

Obst, John, Lignins: Structure and Distribution in Wood and Pulp, USDA Forest Service, Forest Products Laboratory, Madison, Wi., Materials Research Society; 1990; 11–20. vol. 197.

Elsevier Scientific Publishing Company, Lignin, Rodd's Chemistry of Carbon Compounds, Second Edition, vol. III Part D, pp. 271–276, 1976.

Richard M. Wilkins, Biodegradable polymer methods, Controlled Delivery of Crop–Protection Agents, pp. 149–165, 1990.

*Primary Examiner*—S. Mark Clardy
*Attorney, Agent, or Firm*—Arnold, White & Durkee

[57] ABSTRACT

The present invention provides pest control formulations which comprise lignin as well as methods of protecting pest control agents from environmental degradation through the use of lignin. A solubilized lignin solution is prepared by mixing water, lignin, and a pH adjuster to form a solubilized lignin solution having a pH of between about 7 and about 12, preferably between about 8 and about 11, and most preferably between about 9 and about 10. The solubilized lignin solution is then used to prepare the pest control formulation by mixing with pest control agent and a multivalent salt and drying to form a dispersible formulation. The dispersible formulation is mixed with water to form the pest control formulation having resistance to solar degradation. Alternatively, the solubilized lignin solution may be used as an adjuvant by drying and later adding the dried adjuvant to pest control agent and a multivalent salt to form the pest control formulation, or by mixing directly with pest control agent and multivalent salt to form the pest control formulation. When prepared with the lignin adjuvant, the pest control formulation has improved resistance to washoff as well as resistance to solar degradation.

38 Claims, No Drawings

LIGNIN-BASED PEST CONTROL FORMULATIONS

TECHNICAL FIELD OF THE INVENTION

The present invention relates to pest control formulations which are useful in the delivery of pest control agents, an adjuvant for use with a pest control formulation, and a method of protecting a pest control agent from environmental conditions, including washoff and ultraviolet degradation.

BACKGROUND OF THE INVENTION

Myriad approaches have been pursued to control pests. Many of these methods and compositions are directed to the control of pests that attack plants, most notably commercially valuable plants. Although much current agricultural research has pest control as its objective, pest destruction of plants and plant products is still a major problem.

Control of pests of plants, livestock, and households has been accomplished with the aid of chemical and biological agents. Unfortunately, approaches using these agents may fail due to inadequate formulation of the pesticides. In particular, many formulations are adversely affected by normal environmental conditions. For example, rainfall can wash away control agent deposits and sunlight can inactivate the active agent.

Starch, flour and gluten have been studied extensively as materials to encapsulate pesticides. Encapsulation of the pesticides helps to maintain activity by protecting the active ingredient from harmful environmental conditions. Most of this work has been done with granular matrices in efforts to reduce the amount of chemical pesticide needed to control pests or to protect environmentally sensitive pesticides such as biological control agents, and thus extend their activity. While efforts with these granular formulations have been successful, by far the majority of pesticides are applied as sprayable formulations.

Sprayable formulations are essential for the widespread use of biological control agents. In using sprayable formulations, it is desirable to reduce the concentration of chemical pesticides in such formulations to avoid harm to the environment. Formulations that are effective with lower active ingredient rates are possible through the judicious use of protectants, attractants, or other additives that synergize ingredient activity. Current technologies for sprayable systems require a minimum concentration of solids in the formulation in order to be effective (e.g., 2% for a flour/sucrose formulation and 1% for a gluten formulation). For spray applications which require high volumes of water, the amount of solids which must be used is inconveniently large. For example, higher volumes of water are required to obtain adequate coverage of fruit and vegetable crops, e.g., greater than or equal to 400 L/acre (approximately 1,000 L/ha). The amount of solids required for significant improvement of persistence may exceed 4 kg/acre (9.88 kg/ha). This large amount leads to commercialization restrictions because of costs associated with shipping and handling of large amounts of bulky materials. In situations where low volumes of water are used, for example cotton, which requires less than 40 L/acre (100 L/ha), the solids rate is not as much of an issue. Therefore, for a formulation or adjuvant to be useful for the widest variety of applications, it is preferable that a pest control agent be effective regardless of solids concentration or at a low solids concentration.

When pest control agents are applied to target organisms, the pest control agent can be lost due to environmental conditions. In particular, the pest control agent can be washed off the target organism by rain or through the watering of crops. While sprayable systems for delivery of pest control agents are good at delivering the agent, they typically do not provide protection of the pest control agent against wash-off. For example, in a flour/sucrose delivery system, the pest control agent can be washed off the target organism by the next intense rain.

Another method through which pest control agents lose their effectiveness is through radiation inactivation. Typically, ultraviolet (UV) radiation from the sun degrades and/or inactivates pest control agents. While essentially all pest control agents are susceptible to radiation inactivation, biological pest control agents are particularly sensitive to ultraviolet radiation. There is a need for pest control formulations and for adjuvants that are useful in protecting pest control agents against environmental conditions such as rain and radiation inactivation.

SUMMARY OF THE INVENTION

The present invention provides pest control formulations which comprise a lignin-based adjuvant for use in a pest control as well as methods of protecting pest control agents from environmental degradation through the use of lignin.

One pest control formulation of the present invention (termed the "dispersible formulation") is prepared by mixing a solvent such as water, lignin, and a pH adjuster to form a solubilized lignin solution having a pH of between about 7 and about 12, preferably between about 8 and about 11, and most preferably between about 9 and about 10. The pest control agent is then added to the solubilized lignin solution, followed by the addition of a cross-linking agent. The mixture is then dried and powdered to form the dispersible formulation. The powder is believed to be a pest control agent which is encapsulated in a cross-linked lignin matrix. To use the dispersible formulation to protect a target from pests, the dispersible formulation is mixed with a solvent such as water to form a pest control formulation which is in the form of a sprayable mixture. The pest control formulation may then be applied to a target. The dispersible formulation provides a pest control agent having resistance to solar degradation.

An advantage of the dispersible formulation is that the solids level of the pest control formulation prepared using the dispersible formulation can be controlled with ease. The dispersible formulation of the present invention can be dispersed in any desired volume because the dispersible pest control formulation does not dissolve in aqueous solutions. Therefore, all active pest control agent is covered or coated with cross-linked lignin.

Another formulation of the present invention is an adjuvant (termed the "lignin adjuvant") which is prepared by mixing a solvent such as water, lignin, and a pH adjuster to form a solubilized lignin solution having a pH in the range of from about 7 to about 12 preferably from about 8 to about 11, most preferably from about 9 to about 10. Other components such as dispersants (e.g., detergent), attractants, and feeding stimulants may be added at this point. The solubilized lignin solution is then dried to produce the lignin adjuvant. To use the lignin adjuvant to protect a target from pests, the lignin adjuvant is mixed with a solvent such as water and a pest control agent. A cross-linking agent is then added to form a pest control formulation. The pest control formulation may then be applied to the target. The lignin adjuvant provides a pest control formulation having improved resistance to washoff by rainfall as well as resistance to solar degradation.

3

The present invention also provides a method of protecting a pest control agent from environmental conditions. The pest control agent is delivered to a target organism as the dispersible formulation or as a pest control formulation containing the lignin adjuvant. By adhering to the surface of the target organism, the pest control formulations of the present invention protect the pest control agent from solar degradation and from washoff by rainfall.

DETAILED DESCRIPTION OF THE INVENTION

Lignin is the principal constituent of the woody structure of higher plants and acts as a cementing agent to bind the matrix of cellulose fibers together. It is a complex phenylpropyl polymer of substituted cinnamyl alcohols having an amorphous structure and comprising about 18–35% of woody plants. Lignosulfonate is a sulfonate salt of lignin with a molecular weight range of 1,000–20,000 (Hawley's Condensed Chemical Dictionary, N. Irving Sax and Richard Lewis, Sr., eds, Eleventh edition, 1987, Van Nostrand Reinhold, New York). Lignin and lignosulfonate are byproducts of the wood industry and are produced in large quantities in the production of paper and paperboard products.

In 1978, over $15 \times 10^6$ metric tons of alkali lignin and lignosulfonates were produced by the paper industry in the United States alone. In the past, the liquors of the pulping process, containing the lignin, were routinely dumped into rivers as waste. Today, due to greater awareness of the effects of environmental pollution and EPA regulations, lignin is solidified from the pulp liquors and stored as solid wastes.

Throughout the years, considerable effort has been expended in attempts to find productive uses of lignin. Today, lignins are used as binders, fillers, and resin extenders, among other uses. It would be especially valuable to use this abundantly available wood by-product to protect pest control agents from environmental conditions.

In the paper manufacturing process, wood chips are first pulped to release the lignin. Lignosulfonate (lignin sulfite) is produced by cooking wood chips under pressure in a solution of sulfurous acid and a bisulfite salt. The liquor (sulfite waste liquor) from the cooking process contains lignosulfonate salt with the counter-ion being typically, calcium, magnesium, sodium or ammonium. The pulp is further processed into the desired paper product. Water is removed from the liquor to produce lignosulfonate salts. Lignosulfonate, as expected for a salt, is freely soluble in water but insoluble in organic solvents.

Lignin is produced from a wood-pulping process (Kraft process) in which wood chips are cooked in the presence of a strong hydroxide solution and sulfide ions (typically 10% sodium hydroxide and 20% sodium sulfide). Lignin is removed from the wood chips as a lignin salt (typically the sodium salt) and remains in solution in the liquor. If the water is removed from the liquor without the addition of a sufficient amount of acid, a dry powder containing lignin salt is produced. The lignin salt is soluble in water and is known as alkali lignin or lignin. If the pH of the liquor is reduced to 3 or less, the free base form of lignin (free lignin) precipitates out of solution. Free lignin is insoluble in water but is readily soluble in many organic solvents. Free lignin can be solubilized in water by the addition of a sufficient amount of an alkalizing agent to bring the pH of the solution above 7.

When commercially available lignins are dissolved in water, the pH of the resulting solubilized lignin solutions can vary typically between 7 and 14. The variability is due to the degree of neutralization of the pulp liquors. Also available commercially is a non-ionized form of lignin which is insoluble in water. The non-ionized form of lignin can, however, be solubilized in water by the addition of a sufficient amount of an alkalizing agent such as sodium hydroxide or potassium hydroxide to ionize the cinnamyl alcohol residues. The lignins useful in the present invention include both lignin salts and non-ionized lignin that is solubilized by the addition of an alkalizing agent.

Examples of pH adjusters which may be used to prepare the solubilized lignin solution for both the dispersible formulation and the lignin adjuvant are alkalizing agents such as potassium hydroxide, sodium hydroxide, ammonium hydroxide, and sodium phosphate tribasic.

In addition, if a non-ionized form of lignin is utilized to prepare the lignin adjuvant, an alkalizing agent such as sodium hydroxide or potassium hydroxide is added to provide a solubilized lignin formulation with a pH of between about 7 and about 12.

The cross-linking agent used in the preparation of the dispersible formulation and in the pest control formulation containing the lignin adjuvant is preferably a multivalent salt which is capable of cross-linking lignin molecules together. Examples are salts of beryllium, manganese, calcium, strontium, barium, chromium, magnesium, iron, cobalt, nickel, copper, zinc, aluminum and silver. Preferably, the multivalent salt is magnesium chloride, calcium chloride, zinc acetate, barium chloride, or mixtures thereof. Most preferably, the multivalent salt is calcium chloride. The multivalent salt is present in an amount sufficient to form cross-links between lignin molecules and can range from about 0.05 mole per 100 grams lignin to about 2.0 moles per 100 grams lignin, preferably, from about 0.05 mole to about 1.0 mole per 100 grams of lignin, more preferably, from about 0.05 mole to about 0.5 mole multivalent salt per 100 grams of lignin.

Cross-linking of lignin molecules is likely achieved by the formation of ionic bonds between the cation supplied by the multivalent salt and the anionic cinnamyl alcohol residues of the lignin molecules. Upon application of the pest control formulation containing the lignin adjuvant to a target surface (e.g. foliar surface), the effective concentration of lignin increases as the water in the spray droplet begins to evaporate. As the solids content of the droplet increases, lignin molecules cross-link with each other to form a cross-linked lignin film on the target surface. After the film has formed, the film is no longer soluble in water and resists washoff. It is important that cross-linking occur only after application of the pest control formulation containing the lignin adjuvant onto the target surface. If the lignin molecules begin to cross-link prior to application, cross-linked lignin will precipitate out of the solution. Thus, in preparing the either the dispersible formulation or the adjuvant formulation, the order in which the steps are performed may be important. The lignin solution containing solubilized lignin may have to be prepared before the addition of the multivalent salt. If the multivalent salt is added concurrently with water, pH modifying agent, and lignin, local pockets of high concentrations of lignin and multivalent salt may develop causing the lignin molecules to prematurely cross-link. When lignin molecules cross-link prematurely and precipitate out of solution, the lignin adjuvant may be difficult or impossible to use to deliver pesticide to a target organism. Further, cross-linked lignin molecules that precipitate out of solution clog the spray equipment that is typically used to spray the adjuvant and pesticide onto target organisms. To avoid premature cross-linking while still concurrently mixing multivalent salt, water, pH modifying agent, and lignin is to mix them in high speed mixers.

The amount of lignin in a pest control formulation containing the lignin adjuvant can range from about 0.1 g lignin per 100 mL pest control formulation to about 10.0 lignin per 100 mL. A preferred amount of lignin in the pest control formulation is between about 0.2 g per 100 mL and about 5.0 g per 100 mL. An even more preferred amount of lignin is between about 0.5 g per 100 mL and about 2.5 g per 100 mL pest control formulation. Solutions which contain greater than 10 g lignin per 100 mL may begin to cross-link shortly after preparation and thus may be impractical for field usage.

In preparing the pest-control formulation using the lignin adjuvant of the present invention, the pest control agent may also be added at multiple points during the preparation of the lignin solution. Thus, the pest control agent can be premixed with the lignin; dissolved in water prior to the addition of the lignin, or added to the lignin solution before or after the addition of the pH adjuster. Likewise, the pest control agent can be added before, or after adding the multivalent salt.

Examples of pests upon which the pest control formulations of the present invention may be used are plants, animals, or microorganisms. Examples are insects, spiders, nematodes, fungi, weeds, bacteria and other microorganisms. Pest control agents which may be used in the formulations of the present invention are substances that repel or kill a pest or decrease or inhibit the growth, development or destructive activity of a pest. Thus, a pest control agent can be insecticide, a pesticide, a fungicide, a herbicide, antibiotic, an anti-microbial, a recombinant pest control agent and the like. A pest control agent can be a biological or chemical material. Biological materials are living organisms or substances isolated, produced, or otherwise derived from living organisms. Chemical materials are synthetically-prepared compounds or compositions such as thiocarbonates, dinitroanilines, organophosphates, and alachlor. Pesticides, insecticides, herbicides, fungicides, antimicrobials and antibiotics are commercially available. An exemplary list of such substances can be found in U.S. Pat. No. 4,911,952, the disclosure of which is incorporated herein by reference.

Examples of pest control agents useful for pest control formulations prepared using the dispersible formulation or the lignin adjuvant, include Bravo (2,4,5,6-tetrachloro-1,3-dicyanobenzene, a commercial fungicide), Mancozeb (ethylene bis [dithiocarbamato] manganese mixture with ethylenebis [dithio-carbamato] zinc, a commercial fungicide), dimilin (N--{(4-chlorophenyl) aminocarbonyl} -2,6-difluorobenzamide), malathion ([(dimethoxyphosphinothioyl)thio]butanedioicacid diethyl ester), carbaryl (1-naphthalenolmethylcarbamate) and diazinon® (O,O-diethyl O-[6-methyl-2-(1-methylethyl)-4-pyrimidinyl]phosphorothioate); 2,4-D(2,4-dichlorophenoxy-acetate sodium salt), a 2,4-D ester (2,4-dichlorophenoxyacetate isopropyl ester); metolachlor (2-chloro-N-(2-ethyl-6-methylphenyl)-N-(2-methoxy-1-benzene-dicarboxylate); glyphosate (N-(phosphonomethyl) glycine); paraquat (1, 1'-dimethyl-4, 4'-bipyridinium salt); and trifluralin (1, 1, 1-trifluoro-2, b-dinitro-N, N-dipropyl-p-toluidine); *Bacillus thuringiensis* ("*B. thuringiensis*"), Baculoviridae, e.g., *Autographa californica* nuclear polyhedrosis virus, protozoa such as *Nosema spp.*, fungi such as *Beauveria spp.*, and nematodes.

Alternatively a preferred pest control agent is a recombinant pest control agent. As used herein, a recombinant pest control agent is a pest control agent produced by the use of well known recombinant DNA technology (Sambrook, J., Fritsch, E. F., and Maniatis, T., *Molecular Cloning: A Laboratory Manual*, Cold Spring Harbor Laboratory Press, New York, 1989). Recombinant *B. thuringiensis* toxin is a preferred pest control agent.

The use of a recombinant pest control agent, either treated or in a living state, in a lignin-based formulation for pest control provides for improved protection of the pest control agent from environmental conditions. In particular, a pest control agent is protected from being washed away by water and protected from radiation degradation or inactivation by the sprayable lignin-based formulation. The minimalization of ultraviolet damage to a commercially available recombinant *B. thuringiensis* product is further disclosed in Example 4 below. Both Mycogen MVP® and "cream"provide *B. thuringiensis* toxins encapsulated in substantially intact cells. (MVP® is a trademark of Mycogen Corp., San Diego, Calif.) and is produced using a recombinant process wherein the gene for the toxin produced by *B. thuringiensis* is cloned into *Pseudomonas fluorescens* ("*P. fluorescens*"). *P. fluorescens* is then grown to produce the toxin. The *P. fluorescens* is then killed, producing what Mycogen Corporation terms "cream". The cream is incorporated into the final MVP product formulation.

A pest control agent can also be a mixture of two or more agents.

Some pest control agents are susceptible to degradation at certain pH values. When using these sensitive pest control agents, degradation of the pest control agent can be minimized by preparing the lignin adjuvant with an appropriate pH.

A pesticidally effective amount of a pest control agent is an amount sufficient to bring about the desired response (e.g., to repel or kill a pest). When the pest control agent kills the pest, a pesticidally effective amount is that amount which, when in contact with a pest, results in a significant mortality rate of the pest.

The pest control formulations prepared using the lignin adjuvant or dispersible formulation of the present invention may further comprise additives such as dispersants, phagostimulants, attractants, ultraviolet light protectants, preservatives and/or inert fillers. Examples of such additives can be found in U.S. Pat. No. 4,911,952.

In a preferred embodiment, the additive is an attractant or a phagostimulant. An attractant is preferably a volatile substance that attracts a pest to the spray deposit. A phagostimulant is a substance that stimulates ingestion of the spray deposit. A preferred attractant is a pheromone or a volatile feeding attractant such as p-methoxycinnamaldehyde. An exemplary and preferred phagostimulant is cucurbitacin obtained from the powdered, dried root of the buffalo gourd, or Coax®, a feeding stimulant containing cotton seed flour, sugar, vegetable lipid oil and ethyoxylated ester (CCT Corporation, Litchfield Park, Ariz.). Exemplary sugars are mono-, oligo- and polysaccharides containing from about 1 to about 50 saccharide units. In a preferred embodiment, a sugar is a disaccharide such as sucrose, molasses or corn syrup solids.

The pest control formulations of the present invention adhere to any target surface that is susceptible to damage by pests and the pest control formulations can be delivered in any reasonable manner known to those of skill in the art. Preferably, the pest control formulation is sprayed onto an external surface of vegetation or organism that is susceptible to damage by pests. When applied to vegetation or other living organism, the adjuvant formulation and co-applied pest control agent sticks to the external surface of that organism. The pest control formulation of the present invention will also stick to artificial surfaces such as those made of glass, metal, plastic, wood, and the like. In a preferred embodiment, a formulation of the present invention adheres to an external surface of a living organism such as a plant or animal. Where the living organism is a plant, preferred external surfaces are any surfaces susceptible to damage by insects, and disease such as the leaves, petioles stem, branch, trunk, root, flower, fruit, vegetable, and seeds. Where the living organism is an animal, a preferred external surface is skin, fur or hair.

EXAMPLES

The following techniques were used in the Examples:
Preparation of Formulations with *B. thuringiensis*

For laboratory experiments, formulations were mixed prior to each experiment. Technical powder (the material recovered from fermentation that is used as the active ingredient in the fmal formulation) of *B. thuringiensis* subsp. kurstuki (*B. thuringiensis*, 69,000 IU/mg) was supplied by Abbott Laboratories (Chemical and Agricultural Products Division, North Chicago, Ill.) and was used in formulations to provide a final concentration of 13.800 IU/mL for formulations applied to plants. Preliminary assays showed this concentration to be a discriminating dose of *B. thuringiensis* for the respective bioassays for determining insect mortality. Concentrations of *B. thuringiensis* in solutions for plating varied among experiments. Spore plating assays also used formulations that contained *B. thuringiensis* concentrations within this range of activity.

Spore Plating Assay

The concentration of viable bacterial spores in formulations that were exposed to simulated sunlight and rainfall was determined using a spore plating assay in order to demonstrate the ability of the pest control formulation of the present invention to protecting the pest control agent from adverse environmental conditions. The spore plating assay was carried out as follows: Pest control formulations made with *B. thuringiensis* were mixed and 0.1 mL of each formulation was spread separately on 3 microscope slides (25 mm×75 mm×1 mm) and allowed to air dry for about 1 hour. After drying, one slide with each formulation was exposed to simulated sunlight using the Suntest CPS machine, one slide was rinsed with deionized water to simulate washoff by rain, and one slide was not exposed. The Suntest CPS machine (made by Heraeus) is a xenon-based light source that simulates wavelengths and intensity of natural sunlight. Exposure in the Suntest machine consisted of subjecting the dried formulation to light for up to 80 minutes in the machine set at 7.5, although varying exposure times were used among different experiments. Simulating rain consisted of rinsing each slide with 40 mL of water, which drained from a burette in about 2 minutes. After exposure to light or washoff, the slides were placed individually into screw cap conical tubes (50 mL, 29 mm×114 mm) containing 10 mL of 0.1 KOH solution to dissolve the formulation residue from the slide. This solution containing the *B. thuringiensis* spores was serially diluted to $10^{-5}$ and each dilution was plated on nutrient agar. After a 18 hour incubation at 24° C., the number of viable spores was determined by counting bacterial colonies and assuming each colony was initiated by one spore. The percentage of viable spores remaining (% VR) for each of the exposures (light or washoff) was determined based on the number of viable spores determined for the unexposed slide of the corresponding formulation using the equation: Exposed+Not Exposed)×100=% VR.

Droplet Bioassay

A droplet bioassay was used to measure the insecticidal activity of pest control formulations applied to glass slides and exposed to simulated light and rainfall. The droplet bioassay was carried out by mixing the pest control formulations at a concentration of 800.000 International Units (IU, standard measure of activity for *B. thuringiensis*) per mL. Then, 0.1 mL was applied to each of two slides for each treatment. Slides were exposed to light or simulated rainfall, or to neither light nor rainfall, and subsequently dissolved in 10 mL of a solution consisting of 0.1% w/v KOH, 1% w/v sucrose, and 20% v/v green food color to provide a fmal potency of 16,000 IU/mL in the final droplet solution. Neonate (newly hatched larvae) European corn borers were allowed to feed on droplets of this solution. Larvae that fed on the solution were determined based on the green color in their gut and selected for the assay. Selected larvae were transferred to individual cups containing diet and incubated for 3 days. After incubation the number of live and dead larvae were counted and the percentage mortality was determined for each formulation. The percentage of original insecticidal activity remaining (% OAR) was determined by comparing the mortality of the larvae which fed on the exposed formulation to the mortality of those who fed on the unexposed formulation using the equation: (Exposed+Not Exposed)×100=% OAR.

Laboratory Studies

Experiments were conducted in the laboratory to measure rainfastness and solar stability of various adjuvants and formulations. Cotton, *Gossypium hirsutum* L., 'DES 119', plants were grown in a glass house in 15 cm diameter plastic pots. Two plants were grown in each pot in a peat moss-vermiculite soil mixture. When the plants in each pot had five or more fully expanded true leaves, pots were selected and paired for treatments so that each treatment had 10 large true leaves. Cotyledon leaves and immature true leaves were trimmed from the plants. After trimming, the remaining leaves were washed with tap water to remove soil and plant exudates that may interfere with larval survival during the assay. Plants were allowed to dry before the application of formulations.

Method of Application to Plants

Pest control formulations made using lignin were applied to plants in a spray chamber (Research Track Sprayer, DeVries Manufacturing, Hollandale, Minn.). This chamber held up to eight pots of plants on a stationary platform and applied the pest control formulations through a spray apparatus that passed over the plants. Applications were made through a flat fan 8002ss nozzle (Spray Systems, Wheaton, Ill.) at 4.9 kg/cm$^2$ and a track speed setting of 3.0 km/h to apply 36 mL total volume across 2 m of track length. Spray residue was allowed to dry before the application of simulated rain. An untreated control was included with each experiment to assess larval mortality due to handling.

Rainfastness Assay

Rain was simulated by applying 5 cm of tap water at 2.5 kg/cm$^2$ with the same spray chamber fitted with a full jet FL-5VC (Spray Systems co., Wheaton, Ill. spray nozzle. To simulate rain, the traveling spray apparatus continuously traversed the chamber back and forth until the desired amount of rain as measured by a rain gauge placed inside the spray chamber was applied. Plants were allowed to dry overnight before assaying.

Solar Stability Assay

To measure solar stability, 100 μL of formulation or adjuvant was carefully spread onto a 33 cm$^2$ leaf disk which had been marked onto a cotton leaf while still on the plant.

For each treatment, 20 disks were treated. Ten disks received solar treatment and the other 10 remained in the laboratory under ambient light conditions. The solar treatment consisted of placing the cotton plants under a Suntest CPS light source so that all 10 marked leaves were equidistant from the light. A sheet of plastic was placed between the light and the plants to avoid excessive drying of the leaf tissue. Light intensity readings taken with a LiCor solar spectroradiometer demonstrated no loss of energy in the 300–800 nm range due to the plastic cover. Unless otherwise indicated, the exposure time was 20 minutes for formulations containing viruses and 8 hours for all other formulations.

Cotton Leaf Bioassay

Ten circular disks (33 cm²) were cut from the cotton leaves for each treatment. Individual leaf disks were placed treated side down on a filter paper in a 100×15 mm petri dish. Ten neonate European corn borer were transferred to each leaf disk, each dish was sealed with two wraps of parafilm, and dishes were placed in a dark incubator at 27°–30° C. for three days. After incubation, the number of live and dead larvae were counted on each leaf disk and the percentage mortality was calculated. If larval mortality in the control was high (>15%), the mortalities for the treatments were corrected using Abbott's formula.

Insects

European corn borer neonates were used in all experiments to ascertain differences between the pest control formulations of the present invention based on mortality. European corn borer eggs were obtained from a laboratory colony reared according to standard laboratory techniques. The colony was routinely supplemented with weekly shipments of eggs from the USDA-ARS Corn Insects Research Unit, Ames, Iowa.

EXAMPLE 1

Dispersible Formulation

This example demonstrates that the dispersible formulation protects the pest control agent from harmful environmental conditions. A control formulation was prepared by mixing 10 g of kraft lignin in 100 mL water with 1.4 g KOH. Then 1 g of potassium phosphate in 50 mL water was added to the lignin mixture and mixed in a blender to form a solubilized lignin solution. Finally, 10 g of the pest control agent B. thuringiensis was added and the preparation was diluted to 200 mL. A second preparation, the inventive formulation, was prepared in a manner similar to the first with the addition of 1 g calcium chloride as a crosslinking agent. Both control and inventive formulations were spray-dried to microencapsulate the B. thuringiensis in the lignin and thus protect B. thuringiensis from light degradation. The spray dryer used was a Yamato Pulvis mini-spray model GA-31 (Yamato Scientific Co., Ltd., Tokyo, Japan). Drying temperatures were 92° C. inlet temperature and 55° C. outlet temperature with a flow rate of 7 mL/minute. Samples of both control and inventive formulations were also air-dried to verify that the heat of spray-drying did not reduce the spore viability of these formulations. The formulations were then exposed to Suntest light with the spore plating assay to determine spore viability. The results appear in Table 1.

TABLE 1

| Formulation | Drying Process | CFU's/mg of formulation (unexposed) | % VR |
|---|---|---|---|
| Unformulated | — | 920000 | 4 |
| Lignin control | Air dried | 590000 | 53 |
| Lignin control | Spray dried | 460000 | 40 |
| Lignin/CaCl$_2$ | Air dried | 440000 | 47 |
| Lignin/CaCl$_2$ | Spray dried | 560000 | 66 |

Table 1 shows that the determination of colony forming units (CFU's) verified that the spray-drying process did not reduce spore viability. In addition, it shows that the air dried formulation protected spores from light degradation similar to spray dried formulation.

EXAMPLE 2

Dispersible Formulation: UV Protectant Effects

An experiment was done to demonstrate that the spray-dried dispersible formulation of B. thuringiensis retained insecticidal activity on plants after exposure to light. An inventive pest control formulation, spray-dried dispersible formulation prepared as Example 1 and unformulated B. thuringiensis technical powder (which did not contain lignin), were applied to cotton plants with the spray chamber. Plants were then subjected either to 5 cm simulated rain in the rain chamber (rainfastness assay), 8 hours of light in the Suntest machine (solar stability assay), or left unexposed before assaying against neonate European corn borer (cotton leaf bioassay) to determine insecticidal activity of each formulation. The results appear in Table 2.

TABLE 2

| Formulation | Exposure | % Mortality | % OAR |
|---|---|---|---|
| Unformulated | none | 98 | — |
| Unformulated | 8 hour Suntest | 16 | 16 |
| Unformulated | 5 cm water | 15 | 15 |
| Lignin | None | 100 | — |
| Lignin | 8 hour Suntest | 64 | 64 |
| Lignin | 5 cm water | 7 | 7 |

Table 2 shows that both the control (unformulated B. thuringiensis) and the inventive (dispersible formulation B. thuringiensis) formulations had high insecticidal activity when not exposed to light or simulated rainfall and both formulations had low insecticidal activity when exposed to simulated rainfall. However when exposed to light, the spray-dried dispersible formulation retained 64% of its original insecticidal activity compared with 15% for the unformulated B. thuringiensis formulation.

EXAMPLE 3

Dispersible Formulation for a Virus

This example demonstrates that spray-drying lignin with a virus as the pest control agent provides a suitable pest control formulation. Two inventive pest control formulations were prepared. First, a pest control formulation using the dispersible formulation was prepared by adding 5 g lignin to 100 mL water containing 650 mg KOH. Then, 50 mL water containing 1 g KH$_2$PO$_4$ was added to bring the pH to 7.5 to form a solubilized lignin solution. Next, 50 mL water containing 1 g calcium chloride was added. Finally, 5 mL of a virus suspension [containing approximately $10^{10}$ polyhedral inclusion bodies (PIBS)/mL of an insect pathogenic baculovirus isolated from *Autographa california* (designated ACMNPV V8 wild type obtained from American Cyanamid Co.)] was added to this mixture.

The mixtures were then dried by spray-drying in a Niro Atomizer (Niro Inc., Columbia, Md.) to form the dispersible formulation. The spray-drying was carried out at an inlet temperature of 158° C., and an outlet temperature of 81° C. The residence time in the collection vessel was approximately 30 minutes. The yield was 5.62 g with an estimated PIB concentration of $6.2 \times 10^9$ PIBS/g.

Next, a pest control formulation using the lignin adjuvant was prepared by mixing 2.5 g kraft lignin to 250 mL water containing 300 mg KOH to form a solubilized lignin solution. 225 mL water was added and then 22 mL of a solution containing 1% calcium chloride and 0.7% $KH_2PO_4$ was added. A 10 mL sample was taken for use in the assay. 0.01 mL of the virus preparation used to prepare the dispersible formulation which contained approximately $10^{10}$ polyhedral inclusion bodies (PIBS)/mL of an insect pathogenic baculovirus isolated from *Autographa californica* (designated ACMNPV V8 wild type obtained from American Cyanamid Co.) was added to the 10 mL sample. Cotton leaves were treated by adding 0.033 mL to a premarked 11 $cm^2$ circular area and tested in a bioassay.

The bioassay was carried out as follows: third instar *Trichoplusia ni*, cabbage looper, were obtained from a laboratory colony and starved for 24 hours. Leaf disks were removed from the treated cotton leaves with a #2 cork borer (approximately 5 mm diameter; each small leaf disk had $10^5$ PIBS based on the material we added previously) and fed to the starved larvae. After a 24 hour access to the leaf disks, larvae that had consumed the entire disk were transferred to an artificial diet and held for 7 days. Mortality due to virus was then assessed. Abbott's formula was used to correct for control mortality. This experiment was conducted twice. The results appear in Table 3.

TABLE 3

| Formulation | Log Dose | Solar Exposure (minutes) | % Mortality | % OAR |
|---|---|---|---|---|
| Lignin | 7 | 0 | 95 | |
| Lignin | 6 | 0 | 62 | |
| Lignin | 5 | 0 | 22 | |
| Lignin | 4 | 0 | 1 | |
| Lignin | 6 | 20 | 28 | 45 |
| Lignin Adjuvant | 6 | 20 | 63 | 100 |

Table 3 shows an estimated dose/mortality study indicating that, overall, there was a slight loss of activity compared with previous studies. However, the solar stability of the spray dried formulation was greater than that previously seen for naked or unformulated virus applications which showed no insecticidal activity after a 20 minute exposure in the Suntest machine.

EXAMPLE 4

Lignin Adjuvant for *B. thuringiensis*

This example demonstrates that a pest control formulation prepared using the lignin adjuvant of the present invention provides resistance to washoff for several formulations of *B. thurningiensis*: Dipel 2X (Abbott Laboratories), Mycogen MVP (Mycogen Co.), technical powder (Abbott Laboratories), and technical cream (Mycogen Co.). The formulations were prepared with and without lignin adjuvant. A solubilized lignin solution was prepared by dissolving 10 g kraft lignin in 90 mL of water with 1.4 g potassium hydroxide. Then, 10 mL of this solubilized lignin solution was diluted to 100 mL in the final *B. thuringiensis* spray. After mixing the lignin solution with the *B. thuringiensis*, calcium chloride dihydrate (220 mg) was added to each preparation. The eight preparations were applied to cotton plants with the DeVries spray chamber and exposed to washoff (rainfastness assay) by 5 cm of simulated rain. Insecticidal activity for the 16 treatments were determined based on the cotton leaf assay for European corn borer mortality. The results appear in Table 4.

TABLE 4

| Preparation | mg/100 mL | With Lignin Adjuvant | % OAR |
|---|---|---|---|
| Dipel 2X | 40 | no | 47 |
| Dipel 2X | 40 | yes | 96 |
| Mycogen MVP | 160 | no | 9 |
| Mycogen MVP | 160 | yes | 52 |
| Technical powder | 20 | no | 17 |
| Technical powder | 20 | yes | 98 |
| Mycogen cream | 80 | no | 6 |
| Mycogen cream | 80 | yes | 65 |

Table 4 shows that the pest control formulations containing the lignin adjuvant retained the insecticidal activity of each of the *B. thuringiensis* preparations when exposed to simulated rain.

EXAMPLE 5

Washoff Resistance of Lignin Adjuvant

Several concentrations of the lignin adjuvant were compared for resistance to washoff when exposed to simulated rain in cotton leaf bioassay against European corn borer. Lignin adjuvant was prepared as in Example 4 using the technical powder except that the concentration was adjusted to provide 0.25%, 0.50%, 0.75%, and 1.00% w/v of lignin in the pest control formulation (% w/v=g lignin/100 mL pest control formulation). This experiment was conducted twice and the average percent original activity remaining (% OAR) is reported in Table 5. The commercial formulation Dipel 2X was included for comparison.

TABLE 5

| Preparation | % w/v Lignin | % OAR |
|---|---|---|
| Unformulated *B. thuringiensis* | — | 28 |
| Dipel 2X | — | 21 |
| Lignin Adjuvant | 0.25 | 54 |
| Lignin Adjuvant | 0.50 | 63 |
| Lignin Adjuvant | 0.75 | 82 |
| Lignin Adjuvant | 1.00 | 74 |

The 0.75% w/v concentration of lignin adjuvant provided the greatest resistance to washoff with an average of 82% OAR. All treatments containing lignin adjuvant resisted washoff better than unformulated technical powder or the commercial formulation (Dipel 2x).

EXAMPLE 6

Pest control formulations containing different adjuvants were compared for resistance to washoff by simulated rainfall and light degradation of spores when prepared in the adjuvant form. Kraft lignin denotes a specific process used by the pulping industry to remove lignin from the wood pulp and utilizes high temperatures (150°–170° C.) with strong sodium hydroxide in the presence of sulfide ions. Induline® AT kraft pine lignin (Westvaco Chemical Division, Charleston Heights, S.C.) is a purified form of kraft lignin which is free of all hemicellulosic materials. REAX® 907 dispersant lignin (Westvaco Chemical Division, Charleston Heights, S.C.) is a low sulfonated kraft lignin dispersant featuring low-free electrolytic content and low conductivity and near neutral pH. In this experiment, kraft lignin, Indulin, and REAX (10 mg/mL) were solubilized individually in KOH solution and used to make three different solubilized lignin solutions. Calcium chloride (1 mg/mL) and B. thuringiensis (10 mg/mL) were added to each solubilized lignin solution to form pest control formulations. A control preparation of kraft lignin without calcium chloride was included to demonstrate the need for the salt. The lignin adjuvant preparations were subjected to the spore plating assay for resistance to a 40 minute exposure in the Suntest machine or to washoff by 40 mL of water. Results appear in Table 6.

TABLE 6

| Preparation | % VR, Suntest Exposure | % VR Washoff |
| --- | --- | --- |
| Unformulated | 3 | 1 |
| Kraft lignin control | 81 | 1 |
| Kraft Lignin/CaCl$_2$ | 64 | 53 |
| Indulin Lignin/CaCl$_2$ | 56 | 60 |
| REAX Lignin/CaCl$_2$ | 26 | 16 |

Table 6 shows that all pest control formulations were effective at protecting the spore viability from light degradation. However, the kraft lignin control preparation showed no resistance to washoff and demonstrated the need for a multivalent salt (or other mechanism) to cross-link the lignin and provide resistance to washoff.

EXAMPLE 7

B. thuringiensis Concentration

This example shows that a pest control formulation containing the lignin adjuvant was able to protect B. thuringiensis from light degradation and washoff when a wide range of B. thuringiensis concentrations were used. Concentrations of B. thuringiensis ranged from 1.25 mg/mL to 10 mg/mL in pest control formulations prepared with calcium chloride and in a control prepared without calcium chloride. Three formulations which did not contain lignin were also tested: unformulated B. thuringiensis, B. thuringiensis mixed with calcium chloride, and B. thuringiensis mixed with lignosulfonate. The spore plating assay was conducted and all formulations were exposed for 40 minutes in the Suntest machine and to washoff by 40 mL of water. Results appear in Table 7.

TABLE 7

| Preparation | Concentration Rate of B. thuringiensis (mg/mL) | Suntest Exposure (% VR) | Washoff (% VR) |
| --- | --- | --- | --- |
| Unformulated | 50 | 3 | 1 |
| CaCl$_2$ | 50 | 3 | 1 |
| Lignosulfonate | 50 | 31 | 0 |
| Lignin | 12.5 | 40 | 0 |

TABLE 7-continued

| Preparation | Concentration Rate of B. thuringiensis (mg/mL) | Suntest Exposure (% VR) | Washoff (% VR) |
| --- | --- | --- | --- |
| Lignin | 50 | 67 | 1 |
| Lignin | 100 | 60 | 0 |
| Lignin/CaCl$_2$ | 12.5 | 100 | 64 |
| Lignin/CaCl$_2$ | 50 | 16 | 73 |
| Lignin/CaCl$_2$ | 100 | 100 | 77 |

Table 7 indicates that the cross-linking agent may be necessary to provide resistance to washoff. It also shows that while lignosulfonate, a common formulation additive included for comparison purposes, provided protection from Suntest light, it had no resistance to washoff.

EXAMPLE 8

Cross-Linking Agent Concentration

Preparations of pest control formulations containing lignin adjuvant were prepared with varying amounts of cross-linking agent to demonstrate protection from washoff and light degradation of spore viability. Spore viability remaining was determined by the spore plating assay. Dipel 2X (B. thuringiensis) was used as the active ingredient in each of the preparations. A solubilized lignin solution was prepared with 5 g lignin/100 mL dissolved by 0.65 g/100 mL potassium hydroxide. The cross-linking agent calcium chloride was then added at a relative concentration of calcium chloride to potassium hydroxide (CaCl$_2$:KOH) from 0–2. The results appear in Table 8.

TABLE 8

| Preparation | Ratio of CaCl$_2$:KOH | % VR Light Exposure | % VR Washoff |
| --- | --- | --- | --- |
| Dipel | — | 1 | 42 |
| Dipel/Lignin Adjuvant | 0.0:1.0 | 26 | 35 |
| Dipel/Lignin Adjuvant | 0.5:1.0 | 59 | 61 |
| Dipel/Lignin Adjuvant | 1.0:1.0 | 49 | 13 |
| Dipel/Lignin Adjuvant | 1.5:1.0 | 34 | 92 |
| Dipel/Lignin Adjuvant | 2.0:1.0 | 27 | 66 |

Table 8 shows that the greatest resistance to light degradation of spore viability (59% VR) was provided by the pest control formulation prepared with a ratio of 0.5 CaCl$_2$:KOH. The greatest resistance to washoff (92% VR) was provided by the pest control formulation containing lignin adjuvant which had a ratio of 1.5 CaCl$_2$:KOH.

EXAMPLE 9

Lignin Adjuvant for Entomopathogenic Virus

This example demonstrates the effect of pest control formulations containing lignin adjuvants on the survival and insecticidal activity of a baculovirus.

To prepare a solubilized lignin solution, 2.5 g kraft lignin was added to 250 mL water containing 300 mg KOH, then 225 mL water was added. 22 mL of a solution containing 1% calcium chloride and 0.7% KH$_2$PO$_4$ were then added. A 10 mL sample was taken for use in the assay. 0.01 mL virus preparation which contained approximately $10^{10}$ polyhedral inclusion bodies (PIBS)/mL of an insect pathogenic baculovirus isolated from Autographa californica (designated ACMNPV V8 wild type obtained from American Cyanamid Co.) was added to the 10 mL sample. Cotton leaves were treated by adding 0.033 mL to a premarked 11 cm² circular area and tested in a bioassay. In this test, adjuvants other than lignin were tested: flour/sucrose at 2% solids, alkali gluten at 1% solids (pH 11.2), and acidic gluten at 1% solids (pH 3.4).

The bioassay was performed by obtaining third instar *Trichoplusia ni* from a laboratory colony and starving for 24 hrs. Leaf disks were removed from the treated cotton leaves with a #2 cork borer (approximately 5 mm diameter; each small leaf disk had $10^5$ PIBS based on the material we added previously) and fed to the starved larvae. After 24 hour access to the leaf disks, larvae that had consumed the entire disk were transferred to artificial diet and held for 7 days. Mortality due to virus was then assessed. Abbott's formula was used to correct for control mortality. This experiment was done twice. The results appear in Table 9.

TABLE 9

Effect of adjuvant on virus activity.

| | Percentage Mortality | | |
|---|---|---|---|
| Adjuvant | Trial 1 | Trial 2 | Avg. |
| None | 84 | 36 | 60 |
| Lignin | 47 | 50 | 49 |
| Flour/sucrose | 57 | 87 | 72 |
| Gluten/alkali | 5 | 11 | 8 |
| Gluten/acid | 61 | 89 | 75 |

All virus-adjuvant mixtures, except alkali gluten, infected and killed a similar (statistically) number of larvae.

EXAMPLE 10

An experiment was done to determine whether a pest control formulation containing lignin adjuvant would provide solar stability to a virus. A pest control formulation containing the lignin adjuvant was prepared by adding 5 g lignin to a solution containing 650 mg KOH in 250 mL water and mixing in a blender. A 50 mL sample of this mixture was taken and the pH adjusted to 7.3 with 10 mL of a solution containing $KH_2PO_4$. Another 10 mL of a solution containing 200 mg $CaCl_2$ was added and the entire mixture was then diluted to 200 mL. Virus was then added at 10 times the amount used in Example 9. A pest control formulation with flour/sucrose instead of lignin as the adjuvant was prepared for comparison.

Treated leaves were exposed to artificial sunlight from the SunTest machine (as previously described) for 20 minutes. The bioassay was conducted in the same manner as for Example 9 except each larva consumed a leaf disk with $10^6$ PIBS. The results appear in Table 10.

TABLE 10

Effect of Adjuvants on Solar Stability of Virus

| Adjuvant | Exposure Period | Percentage mortality | OAR |
|---|---|---|---|
| None | 0 | 91 | |
| None | 20 | 0 | 0 |
| Lignin | 0 | 100 | |
| Lignin | 20 | 54 | 54 |
| Flour/sucrose | 0 | 100 | |
| Flour/sucrose | 20 | 46 | 46 |

Table 10 shows that pest control formulations prepared using lignin and flour/sucrose both provided significant protection from simulated sunlight (Table 10).

EXAMPLE 11

An experiment was done to demonstrate the extent to which a pest control formulation containing the lignin adjuvant of the present invention can protect an entomopathogenic virus from solar degradation.

The pest control formulation containing the lignin adjuvant was prepared as in Leaves treated with the pest control formulation were then exposed to simulated sunlight for 0, 10, 20, 40, or 80 minutes. The bioassay was done in the same manner as for Example 9.

TABLE 11

| Adjuvant | Exposure Period | % Mortality | % OAR |
|---|---|---|---|
| None | 0 | 100 | — |
| Lignin | 0 | 84 | — |
| Lignin | 10 | 42 | 51 |
| Lignin | 20 | 49 | 59 |
| Lignin | 40 | 13 | 16 |
| Lignin | 80 | 16 | 19 |

Table 11 shows that the pest control formulation containing the lignin adjuvant provided suitable protection for the virus (>50% OAR) for up to 20 minutes.

EXAMPLE 12

Lignin Adjuvant for Fungicide

This example demonstrates that a pest control formulation containing the lignin adjuvant protects a chemical pesticide from washoff by simulated rain. A solubilized lignin solution was prepared by dissolving kraft lignin (10 g) in water (100 mL) containing potassium hydroxide (1.4 g) and detergent (4 mL Joy®). This solubilized lignin solution was then dried, ground, and sieved to pass a 60 mesh screen to form the lignin adjuvant. The lignin adjuvant (150 mg) was dissolved in water (5 mL) and mixed with a non-systemic protectant fungicide (Tilt: 7-bromo-5-chloroquinolin-8-yl-acrylate) at a concentration of 1 g Tilt in 15 mL water, and calcium chloride solution (3%, 1 mL). A rainfastness assay was conducted wherein five drops of this mixture was spread on each of four microscopic glass slides and allowed to air dry. After drying, half of the slides were rinsed under a stream of water (about 100 mL in about 20 seconds). The slides were allowed to dry and the Tilt was then extracted with n-dioxane (5 mL). The concentration of Tilt was measured spectophotometrically and results were compared between rinsed and unrinsed samples. The recovery was 90.6% when Tilt was applied to the slide with pest control formulation containing lignin adjuvant compared to 0.0% recovery when Tilt was applied to the slide without lignin adjuvant.

EXAMPLE 13

An experiment was done to demonstrate the effectiveness of lignin adjuvant in providing rainfastness to a commercial fungicide (Bravo™(2,4,5,6-tetrachloro-1,3-dicyanobenzene) when a pest control formulation containing the lignin adjuvant and the commercial fungicide is applied to banana leaves (*Musa acuminata*). A solubilized lignin solution (1.25 mg, 62 mg, and 31 mg, respectively) as described in Example 12 was used as the lignin adjuvant and was mixed in 5 mL of a fungicide solution (5%) to prepare three fungicide/lignin adjuvant solutions. After the lignin dissolved, 1 mL of calcium chloride (3%) was added to each. The rainfastness assay was conducted as follows: Rectangular areas 15 mm×75 mm were marked on a banana leaf and 0.1 mL of each preparation was spread evenly on two marked areas. One area with each preparation was rinsed in the DeVries spray chamber with 5 cm simulated rain while the other was not treated with simulated rain. After application of the rain treatment, treated leaf sections were excised and the Bravo fungicide was extracted from the leaf with 10 mL n-dioxane. A sample from each extraction solution was analyzed for the concentration of fungicide by gas chromatography and peaks were identified by a mass series selective detector using standard techniques. The percentage of fungicide remaining after exposure to simulated rain was determined by comparing the rain exposed to the non-exposed sample for each preparation. The results are shown in Table 12.

TABLE 12

| Amount of Lignin (mg/mL) | % Fungicide Remaining After Rain |
|---|---|
| None | 17 |
| 5 | 100 |
| 12 | 98 |
| 23 | 73 |

Table 12 shows that fungicide alone was ineffective at resisting washoff from the leaf with 17% remaining after the 5 cm simulated rain. However, all preparations of fungicide/ lignin adjuvant were effective at resisting washoff with greater than 70% of the fungicide remaining on the leaf after rain exposure.

EXAMPLE 14

An experiment was done to test the rainfastness of a pest control formulation containing the lignin adjuvant and a fungicide applied to bananas in Central America. Vondozeb 75% DG (containing the active ingredient Manganese zinc salt of ethylene bis-dithiocarbamate also known as "mancozeb") is a pesticide that is applied to bananas during the dry season to prevent fungal infection. Currently, Vondozeb is applied with a sticking agent (NuFilm adjuvant; active ingredient poly-1-p-menthene) to protect the pest control agent from washoff and is known to wash off the plants during the frequent rains that occur in the banana growing areas, even in the dry season. To resist this washoff, a tank mix was prepared containing the amount of Vondozeb recommended by the manufacturer (15% w/v) and lignin adjuvant (4% w/v). Vondozeb with lignin adjuvant and Vondozeb with NuFilm adjuvant were applied to banana leaves and fruit and observed seven days later for phytotoxicity and pesticide residue. No phytotoxic reaction was observed on the fruit or the leaves from either pesticide application. Residue was observed on the fruit and leaves treated with the Vondozeb/lignin adjuvant treatment but no residue was observed on the leaves treated with Vondozeb/ NuFilm adjuvant treatment. This example shows that the lignin adjuvant of the present invention is effective at resisting washoff in a field situation with natural rainfall. It further shows that low volume pesticide applications with high concentrations of active agent can benefit from use of lignin adjuvant to resist washoff.

EXAMPLE 15

Method to Prepare Lignin Adjuvant

A pest control formulation containing lignin adjuvant was prepared by dissolving REAX lignin (100 g) in KOH solution (13 g/400 mL) to form a solubilized lignin solution. After the lignin dissolved, detergent (20 mL Joy®) was added to the solution. The solution was diluted to a concentration of 10 g lignin/100 mL water and spray dried in a Niro Atomizer (Niro Inc., Columbia, Md.) to form the lignin adjuvant. The spray dried powder had smaller particle size than powder produced previously by air drying and hand grinding. The spray dried powder was mixed with granular sugar (25% w/w) and ground together. Adding the sugar provided two benefits. First, the sugar improved the dispersability of the fine powder when added to water. Second, the sugar acted as a phagostimulant for many insects and may have helped to improve the efficacy of stomach poisons for insect control.

EXAMPLE 16

The spore plating assay was conducted to show the benefits of combining the lignin adjuvant with the dispersible formulation of the present invention in the ability to resist photolysis and washoff. The dispersible formulation of the present invention prepared as in Example 15 was compared to a commercial Dipel 2X formulation with and without the addition of a lignin adjuvant of the present invention added to each formulation. The formulations were prepared at concentrations suitable for field application. Field rates of B. thuringiensis are equivalent to 5.79 billion IU/ha (e.g. 181 g Dipel 2X/ha @ 32,000 IU/mg; 210 g Lignin formulated B. thuringiensis/ha @ 27,600 IU/mg). Both forms of B. thuringiensis were made with and without lignin adjuvant at 0.5% w/v (0.5 g/100 mL total volume).

Each of the four treatments was applied to three glass slides (0.1 mL/slide). For each treatment, one slide was exposed to Suntest CPS simulated sunlight for 80 minutes, one was rinsed with 40 mL of water and one was left untreated. After treatment, spores of B. thuringiensis were removed from the slides, diluted, and plated on nutrient agar to determine the relative number of viable bacterial spores remaining for each treatment after exposure. Table 13 contains the results of this laboratory assay.

TABLE 13

| Formulation | Adjuvant | % VR Light Exposure | % VR Wash-off |
|---|---|---|---|
| Lignin | none | 47.2 ± 4.7 | 4.6 ± 6.4 |
| Lignin | Lignin | 69.0 ± 15.7 | 67.0 ± 37.0 |
| Dipel 2X | none | 11.7 ± 6.9 | 14.6 ± 7.7 |
| Dipel 2X | Lignin | 16.4 ± 0.4 | 41.8 ± 15.2 |

Table 13 shows that based on viable spore counts, the pest control formulation containing the lignin adjuvant of the present invention resisted photolysis better than Dipel 2X when exposed to simulated sunlight. Also, lignin adjuvant effectively prevented washoff better than B. thuringiensis formulations containing no adjuvant.

EXAMPLE 17

A pest control formulation containing B. thuringiensis formulated with lignin adjuvant was compared with Dipel 2X without lignin adjuvant for residual insecticidal activity when applied to field grown cabbage and exposed to natural sunlight. Insecticidal activity was determined using a bioassay against newly hatched cabbage looper larvae (Trichoplusia ni, Hhbner). Treatments of each formulation were applied at field rates equivalent to 16 billion IU/acre (approximately 39 billion IU/ha). Original insecticidal activity of the pest control formulation containing the lignin adjuvant and Dipel 2X was not significantly different (LSD P >0.05). After seven days of exposure to sunlight, the lignin formulated *B. thuringiensis* retained 52% of its original insecticidal activity compared with 27% of the original activity remaining for commercial formulation, Dipel 2X. This example illustrates that the lignin adjuvant formulation extended the residual insecticidal activity of *B. thuringiensis* when exposed to natural sunlight.

EXAMPLE 18

An experiment was done to determine the effect of different cross-linking agents on the rainfastness of both the dispersible formulation and the lignin adjuvant formulation. The formulations were prepared with technical *B. thuringiensis* and 1 gram lignin at a total volume of 200 mL. Formulation 1 consisted of *B. thuringiensis* only. Formulations 2–5 were prepared mixing lignin with a pH adjuster (KOH) to form a solubilized lignin solution. *B. thuringiensis* was then added to the solution. Formulations 6 and 7 were prepared in the same manner except that the solubilized lignin solution was dried before mixing with *B. thuringiensis*. The formulations were compared for resistance to washoff when exposed to simulated rain in cotton leaf bioassay against European corn borer. The results in Table 14 show the percent mortality and average percent original activity remaining (% OAR) based upon 10 leaves treated with each formulation. The untreated control had 0% mortality.

TABLE 14

| Formula-tion | Form of lignin | Cross-linking Agent | Mortality (%) No rain | Mortality (%) Rain | OAR (%) |
|---|---|---|---|---|---|
| 1 | none | none | 96 | 28 | 29 |
| 2 | lignin adjuvant | CaCl$_2$.2H$_2$O (250 mg) | 86 | 65 | 76 |
| 3 | lignin adjuvant | BaCl$_2$.2H$_2$O (400 mg) | 40 | 61 | 100 |
| 4 | lignin adjuvant | Zn acetate.2H$_2$O (375 mg) | 92 | 21 | 23 |
| 5 | lignin adjuvant | MgCl$_2$.6H$_2$O (350 mg) | 68 | 87 | 100 |
| 6 | dried lignin adjuvant | CaCl$_2$.2H$_2$O (250 mg) | 54 | 52 | 96 |
| 7 | dried lignin adjuvant | Zn acetate.2H$_2$O (375 mg) | 54 | 66 | 100 |

*One run only.

The experiment was repeated for formulations 1–5. The results appear in Table 15. The results are an average of two runs except where noted.

TABLE 15

| Formula-tion | Form of lignin | Cross-linking Agent | Mortality (%) No rain | Mortality (%) Rain | OAR (%) |
|---|---|---|---|---|---|
| 1 | none | none | 95 | 23 | 19 |
| 2 | lignin adjuvant | CaCl$_2$.2H$_2$O (250 mg) | 92 | 66 | 73 |
| 3 | lignin adjuvant | BaCl$_2$.2H$_2$O (400 mg) | 56 | 55 | 85 |
| 4 | lignin adjuvant | Zn acetate.2H$_2$O (375 mg) | 76* | 43* | 57* |
| 5 | lignin adjuvant | MgCl$_2$.6H$_2$O (350 mg) | 81 | 80 | 89 |

*One run only.

The untreated control had 3% mortality. The results in Tables 14 and 15 show that various salts may be used as cross-linking agents.

We claim:

1. A pest control formulation prepared by the process comprising the steps of:
   (a) mixing water, lignin, and a pH adjuster to form a solubilized lignin solution having a pH of between about 7 and about 12;
   (b) mixing a multivalent salt in an amount sufficient to crosslink said lignin and within the range of about 0.05 to about 0.5 mol per 100 grams of lignin and a pesticidally effective amount of a pest control agent with the solubilized lignin solution;
   (c) drying the mixture of (b) to form a dispersible formulation;
   (d) adding water to the dispersible formulation to form the pest control formulation.

2. The pest control formulation of claim 1 wherein the pH of the solubilized lignin solution is between about 8 and about 11.

3. The pest control formulation of claim 2 wherein the pH of the solubilized lignin solution is between about 9 and about 10.

4. The pest control formulation of claim 1 wherein the multivalent salt is chosen from the group consisting of the salts of beryllium, magnesium, calcium, strontium, barium, chromium, manganese, iron, cobalt, nickel, copper, zinc, aluminum, and silver.

5. The pest control formulation of claim 4 wherein the multivalent salt is calcium chloride, magnesium chloride, zinc acetate, barium chloride, or mixtures thereof.

6. The pest control formulation of claim 5 wherein the multivalent salt is calcium chloride.

7. The pest control formulation of claim 5 wherein the multivalent salt is magnesium chloride.

8. The pest control formulation of claim 1 wherein the pest control agent is 2,4,5,6-tetrachloro-1,3-dicyanobenzene, ethylene bis [dithiocarbamato] manganese, ethylenebis [dithio-carbamato] zinc, dimilin, malathion, carbaryl, O,O -diethyl O-[6-methyl-2-(1-methylethyl)-4-pyrimidinyl] phosphorothioate, 2,4-dichlorophenoxyacetate sodium salt, 2,4-dichlorophenoxyacetate isopropyl ester, metolachlor, glyphosate, paraquat, trifluralin, *Bacillus thuringiensis*, recombinant *Bacillus thuringiensis* toxin, Baculoviridae, a protozoa, a fungus, or a nematode.

9. The pest control formulation of claim 8 wherein the pest control agent is *Bacillus thuringiensis*.

10. The pest control formulation of claim 8 wherein the pest control agent is *Nosema spp*.

11. The pest control formulation of claim 8 wherein the pest control agent is *Beauveria spp*.

12. The pest control formulation of claim 8 wherein the pest control agent is ethylene bis [dithiocarbamato] manganese.

13. The pest control formulation of claim 8 wherein the pest control agent is ethylenebis [dithio-carbamato] zinc.

14. pest control formulation of claim 8 wherein the pest control agent is a Baculoviridae.

15. A method of applying pest control agent to an organism comprising spraying the pest control formulation of claim 1 onto an external surface of the organism.

16. A pest control formulation prepared by the process comprising mixing a lignin adjuvant with water, a multivalent salt in an amount sufficient to crosslink said lignin and within the range of about 0.05 to about 0.5 mol per 100 grams of lignin, and a pesticidally effective amount of pest control agent;

wherein the lignin adjuvant is prepared by the process comprising:

(a) mixing water, lignin, and a pH adjuster to form a solubilized lignin solution having a pH in the range of from about 7 to about 12; and (b) optionally, drying the solubilized lignin solution.

17. The pest control formulation of claim 16 wherein the pH of the solubilized lignin solution is between about 8 and about 11.

18. The pest control formulation of claim 17 wherein the pH of the solubilized lignin solution is between about 9 and about 10.

19. The pest control formulation of claim 16 wherein the multivalent salt is chosen from the group consisting of the salts of beryllium, magnesium, calcium, strontium, barium, chromium, manganese, iron, cobalt, nickel, copper, zinc, aluminum, and silver.

20. The pest control formulation of claim 19 wherein the multivalent salt is calcium chloride, magnesium chloride, zinc acetate, barium chloride, or mixtures thereof.

21. The pest control formulation of claim 20 wherein the multivalent salt is calcium chloride.

22. The pest control formulation of claim 20 wherein the multivalent salt is magnesium chloride.

23. The pest control formulation of claim 16 wherein the pest control agent is 2,4,5,6-tetrachloro-1,3-dicyanobenzene, ethylene bis [dithiocarbamato] manganese, ethylenebis [dithio-carbamato] zinc, dimilin, malathion, carbaryl, O,O-diethyl O-[6-methyl-2-(1-methylethyl)-4-pyrimidinyl] phosphorothioate, 2,4-dichlorophenoxyacetate sodium salt, 2,4-dichlorophenoxyacetate isopropyl ester, metolachlor, glyphosate, paraquat, trifluralin, *Bacillus thuringiensis*, recombinant *Bacillus thuringiensis* toxin, Baculoviridae, a protozoa, a fungus, or a nematode.

24. The pest control formulation of claim 23 wherein the pest control agent is *Bacillus thuringiensis*.

25. The pest control formulation of claim 23 wherein the pest control agent is *Nosema spp*.

26. The pest control formulation of claim 23 wherein the pest control agent is *Beauvera spp*.

27. The pest control formulation of claim 23 wherein the pest control agent is ethylene bis [dithiocarbamato] manganese.

28. The pest control formulation of claim 23 wherein the pest control agent is ethylenebis [dithiocarbamato] zinc.

29. The pest control formulation of claim 23 wherein the pest control agent is a Baculoviridae.

30. The pest control formulation of claim 16 wherein the amount of lignin ranges from about 0.1 g lignin per 100 mL pest control formulation and about 10.0 g lignin per 100 mL pest control formulation.

31. The pest control formulation of claim 30 wherein the amount of lignin ranges from about 0.2 g lignin per 100 mL pest control formulation and about 5.0 g lignin per 100 mL pest control formulation.

32. The pest control formulation of claim 31 wherein the amount of lignin ranges from about 0.5 g lignin per 100 mL pest control formulation and about 2.5 g lignin per 100 mL pest control formulation.

33. A method of applying pest control agent to an organism comprising spraying the pest control formulation of claim 16 onto an external surface of the organism.

34. A method of preparing a pest control formulation comprising the steps of:

(a) mixing water, lignin, and a pH adjuster to form a solubilized lignin solution having a pH of between about 7 and about 12;

(b) mixing a multivalent salt in an amount sufficient to crosslink said lignin and within the range of about 0.05 to about 0.5 mol per 100 grams of lignin and a pesticidally effective amount of a pest control agent with the solubilized lignin solution;

(c) drying the mixture of (b) to form a dispersible formulation;

(d) adding water to the dried dispersible formulation to form the pest control formulation.

35. A method of imparting radiation resistance to a pest control agent comprising incorporating the pest control agent in pest control formulation containing lignin; wherein the pest control formulation is prepared by the process of claim 34.

36. A method of preparing a pest control formulation comprising mixing a lignin adjuvant with water, a multivalent salt in an amount sufficient to crosslink said lingnin and within the range of about 0.05 to about 0.5 mol per 100 grams of lignin, and a pesticidally effective amount of pest control agent;

(a) mixing water, lignin, and a pH adjuster to form a solubilized lignin solution having a pH in the range of from about 7 to about 12; and (b) optionally, drying the solubilized lignin solution.

37. A method of imparting radiation resistance to a pest control agent comprising incorporating the pest control agent in pest control formulation containing lignin; wherein the pest control formulation is prepared by the process of claim 36.

38. A method of imparting resistance to washoff to a pest control agent comprising incorporating the pest control agent in pest control formulation containing lignin; wherein the pest control formulation is prepared by the process of claim 36.

* * * * *

UNITED STATES PATENT AND TRADEMARK OFFICE
CERTIFICATE OF CORRECTION

PATENT NO.: 5,750,467

DATED: May 12, 1998

INVENTOR(S): Shasha et al.

It is certified that errors appear in the above-identified patent, and that said Letters Patent is hereby corrected as shown below.

Column 21, Claim 14, line 3, after "14." insert --The--.

Column 21, Claim 26, line 54, delete "*Beauvera*" and insert --*Beauveria*--.

Column 21, Claim 28, line 59, delete "dithiocarbamato" and insert --dithio-carbamato--.

Signed and Sealed this

Twenty-eighth Day of July, 1998

Attest:

BRUCE LEHMAN

*Attesting Officer*     *Commissioner of Patents and Trademarks*